United States Patent [19]

Saarma et al.

[11] Patent Number: 5,589,625
[45] Date of Patent: Dec. 31, 1996

[54] TRANSGENIC PLANTS DISPLAYING MULTIPLE VIRUS RESISTANCE AND A PROCESS FOR THEIR PRODUCTION

[75] Inventors: Mart Saarma, Helsinki, Finland; Merikke Kelve; Erkki Truve, both of Tallin, Estonia; Teemu Teeri, Espoo, Finland

[73] Assignee: Kemira Oy, Biotech, Helsinki, Finland

[21] Appl. No.: 374,229

[22] Filed: Jan. 18, 1995

Related U.S. Application Data

[63] Continuation-in-part of Ser. No. 965,343, Oct. 23, 1992, abandoned.

[30] Foreign Application Priority Data

Mar. 18, 1992 [EP] European Pat. Off. .............. 92104676

[51] Int. Cl.$^6$ .............................. A01H 5/00; C12N 15/82
[52] U.S. Cl. .................... 800/205; 435/69.1; 435/172.3; 435/240.4
[58] Field of Search ........................ 800/205; 435/172.3, 435/69.1, 240.4, 240.49; 536/23.1

[56] References Cited

PUBLICATIONS

Truve, et al., *Transgenic Potato Palnts Expressing Mammalian 2'5–5'Oligoadenylate Synthetase are Protected From Potato Virus X Infection Under Field Conditions*, Biotechnology, vol. 11, Sep. 1993, pp. 1048–1052.

Truve, et al., *Principles and background for the construction of transgenic plants displaying multiple virus resistance*, Arch Virol (1994) [Suppl] 9:41–50.

Rutherford, et al., *The murine 2–5A synthetase locus: three distinct transcripts form two linkd genes*, Nucleic Acids Research, vol. 19, No. 8, pp. 1917–1924, (1991).

Potrykus, Ingo, *Gene Transfer to Cerals: An Assessment*, BioTechnology, vol. 8, pp. 535–542, Jun. 1990.

Devash, et al., *5'-Dephosphorylated 2',5'-Adenylate Trimer and Its Analogs*, The Journal of Biological Chemistry, vol. 259, No. 6, Issue of March 25, pp. 3482–3486, 1984.

Babosha, et al., Biological Abstracts, Ref. No. 66022, vol. 91 (1991).

Schröder, et al., *Protection of HeLa–T4$^+$ cells against human immunodeficiancy virus (HIV) infection after stable transfection with HIV LTR–2°,5'-Oligoadenylate synthetase hybrid gene*[1], Research Communications, vol. 4, pp. 3124–3130, Oct. 1990.

Sela, et al., *Resistance systems related to the N gene and their comparison with interferon*, 1987 Plant Resistance to Viruses., Wiley, Chichester (Ciba Foundation Symposium 133) P 109–119.

Gelvin, Stanton, *Accurate expression of genes in transgenic plants: do fundamental differences exist between eukaryotes?*, Plant Molecular Biology, 8:355–359, (1987).

*Primary Examiner*—Douglas W. Robinson
*Assistant Examiner*—Elizabeth F. McElwain
*Attorney, Agent, or Firm*—Fish & Richardson P.C.

[57] ABSTRACT

This invention discloses transgenic plants, such as transgenic tobacco and potato, having resistance to multiple viral taxonomic groups using parts of the 2,5A oligoadenylate pathway. In particular, said plants are genetically engineered to contain a DNA sequence encoding at least one polypeptide having a 2,5A synthetase activity. By this means a step in the 2,5A oligoadenylate pathway heretofore believed to be missing in all plants is provided so that viral infection in the transgenic plants is inhibited via a 2,5A dependent endonuclease. Moreover, this invention relates to a process for the production of said transgenic plants by transfection with a genetically engineered DNA sequence encoding at least one polypeptide having a 2,5A synthetase activity.

24 Claims, 9 Drawing Sheets

TRANSGENIC PLANTS DISPLAYING MULTIPLE VIRUS RESISTANCE AND A PROCESS FOR THEIR PRODUCTION

This application is a Continuation-in-Part application of U.S. Ser. No. 07/965,343, filed Oct. 23, 1992, now abandoned.

BACKGROUND OF THE INVENTION

1. Field of the Invention

This invention relates to transgenic plants that are genetically engineered to contain a DNA sequence encoding at least one polypeptide having a 2,5A synthetase activity thereby providing to said plants resistance against multiple taxonomic virus types. Moreover, this invention relates to a process for the production of said transgenic plants and to the use of said genetically engineered DNA sequence.

2. Description of Related Art

Several methods for the construction of virus resistant plants are described in the state of the art. Genetically engineered resistance to a number of plant viruses has been reported by expressing coat protein of a respective plant virus in transgenic plants (Beachy, et al., *Annu. Rev. Phytopathol.*, 28:451–474, 1990).

A substantial virus-resistance to several plant viruses has also been demonstrated by expression of specific viral antisense RNA in transgenic plants (Cuozzo, et al, *Bio/Technology*, 6:549–557 1988; Hemenway, et al., *EMBO J.*, 7: 1273–1280, 1988). The viral antisense RNA exhibits its function either by hybridizing to specific viral DNA or RNA sequences and thus blocking further reactions which are important for the virus propagation, or by ribozyme activity which results in a specific cleavage of viral RNA upon hybridization to said viral RNA.

The main drawback of the above mentioned methods for the construction of virus-resistant transgenic plants is that said transgenic plants are resistant to only one virus or a specific taxonomic group of viruses.

The 2,5A oligoadenylate pathway is part of the antiviral response system induced by interferons in mammalian cells (Lengyel, *Annu. Rev. Biochem.*, 51:251–282, 1982). The key enzyme of the pathway, the 2,5A synthetase, polymerizes ATP to a family of oligonucleotides, the 2,5A. Virus replication is inhibited due to the degradation of viral RNA by the specific 2,5A-activated ribonuclease, RNase L.

In the mammalian system, the 2,5A synthetase polymerizes ATP in the presence of double-stranded RNA (dsRNA, for example replicative intermediates of RNA viruses) to produce a family of oligonucleotides with the general structure $PPP(A2'p5')_nA$ with $n \geq 2$, abbreviated 2,5A. These oligonucleotides possess 2'-5' phosphodiester bonds that are unusual in comparison with ordinary 3'-5' links in the nucleic acids. Two other enzymes involved in the 2,5A system are: (i) 2'-5' phosphodiesterase, which degrades 2,5A, and (II) 2,5A-dependant ribonuclease (RNase L). The 2,5A synthetase is expressed as a inactive enzyme. For its activation, the presence of dsRNA is required. Only dsRNA molecules having a length of at least about 50 base pairs and with no more than one mismatch per 45 nucleotides can activate the synthesis of 2,5A (M. A. Minks, et al., *J. Biol. Chem.*, 254:10180–10183, 1979). Viral RNA has been shown to be a very potent activator of the 2,5A pathway (P. Lengyel, J. Interferon Res. 7:511–519, 1987). Actually, 2,5A is not a single compound, but a mixture of oligoadenylates with different chain lengths and states of phosphorylation. Oligomers with at least three residues are required to activate RNase L. Another requirement for 2,5A activation of RNase L in mammalian cells is a 5' di- or tri-phosphate group. The existence of nonphosphorylated "core" 2,5A molecules in cells also has been reported, but they neither bind to nor activate the RNase L. Activation of the RNase L in mammalian cell extracts is observed already at nanomolar concentrations of 2,5A (I. M. Kerr, *J. Interferon Res.*, 7:505–510, 1987). Due to the activity of 2'-5'-phosphodiesterase in cells, the activation of the 2,5A-dependent RNase is transient without the persistent de novo synthesis of 2,5A.

At least some components of the 2,5A pathway have been detected in organisms other than mammals such as birds, reptilia and amphibia, insects, yeasts and even bacteria (Stark, et al., *Nature*, 278:471–473, 1979; Cayley, et al., *Biochem. Biophys. Res. Comm.*, 108:1243–1250, 1982; Laurence, et al., *Proc. Natl. Acad. Sci. U.S.A.*, 81:2322–2326, 1984).

In plants, an antiviral factor (AVF), the production of which is stimulated by virus infection, was partially purified and its gene appeared to be homologous to human β-interferon; Sela, et al., in: Plant resistance to Viruses: *Ciba Symposium*, No. 133 pp. 109–119, 1987. Treatment of tobacco mosaic virus (TMV)-infected tobacco protoplasts with human interferon led to the inhibition of TMV-replication; Sela, *Methods in Enzymology*, 119:744–752, 1986. Moreover, it has been demonstrated that 2,5A can inhibit TMV replication in tobacco plants; Devash, et al., *J. Biol. Chem.*, 259:3482–3486, 1984. DNA sequences homologous to human 2,5A synthetase were also found in tobacco genomic DNA; Sela, supra. The absence of $(2'-5')pppA_nA$-binding proteins in plants has been independently demonstrated (P. J. Cayley, et al., *Biochem Biophys. Res. Commun.*, 108:1243–1250, 1982). Furthermore, it has been reported that interferon produced in transgenic plants does not inhibit virus propagation; De Zoeten, et al., *Virology*, 172:213–222, 1989.

A 2,5A dependent RNAse, which is part of the 2,5A oligoadenylate pathway in mammals, has not yet been reported in plants in the state of the art. This has led to the conclusion that 2,5A does not inhibit virus infection in plants via a 2,5A dependent endonuclease; Devash, et al., *Biochemistry*, 24:593–599, 1985. A probe of the human 2-5A synthetase was shown to hybridize to tobacco genomic DNA and mRNA from TMV infected tobacco (I. Sela, et al. in: Evered D., et al. Eds., *Plant Resistance to Viruses.*, J. Wiley, Chichester, pp 109, 119, 1987), although 2,5A synthetase activity had not been detected in tobacco earlier (Cayley, supra). The partially purified ATP-polymerizing plant enzyme also reacted with antibodies to human 2,5A synthetase (Sela, et al., supra). Recently, exogeneous nonphosphorylated 2-5 A molecules longer than trimers were demonstrated to induce both increased cytokinin activity and the synthesis of pathogenesis-related and heat shock proteins in tobacco and wheat (O. N. Kulacva, et al., *Plant Mol. Biol.*, 20:383–393, 1992).

In summary, the prior art does not permit the conclusion that the 2,5A oligoadenylate pathway can be used as a basis for constructing transgenic plants displaying multiple virus resistance. Thus, the technical problem of the present invention is to provide a transgenic plant displaying resistance to multiple virus taxonomic groups using parts of the 2,5A oligoadenylate pathway.

The solution to the above technical problem is achieved by providing the embodiments characterized in the claims.

One object of the present invention relates to a transgenic plant displaying multiple virus resistance which contains a genetically engineered DNA sequence encoding at least one polypeptide having a 2,5A synthetase activity, wherein said polypeptide upon expression is capable of activating an endonuclease causing degradation of viral RNA.

SUMMARY OF THE INVENTION

In the present invention a transgenic plant is provided that displays resistance to multiple viral taxonomic groups. The transgenic plant contains a genetically engineered DNA sequence encoding at least one polypeptide having a 2,5A synthetase activity, wherein the polypeptide activates an endonuclease contained within the plant, thereby causing degradation of viral RNA so as to prevent or lessen infection. The invention also discloses propagating material derived from such transgenic plants.

In an alternative embodiment, a process is provided for the production of a transgenic plant having resistance to multiple viral taxonomic groups by transfection with a genetically engineered DNA sequence that encodes a polypeptide have a 2,5A synthetase activity wherein the polypeptide is capable of activating an endonuclease that causes degradation of viral RNA.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

FIG. 3 contains two graphs showing the effect of differently phosphorylated forms of 1γM 2,5A on TMV RNA in vitro translation in wheat germ extract.

DETAILED DESCRIPTION OF THE INVENTION

Figure 1:
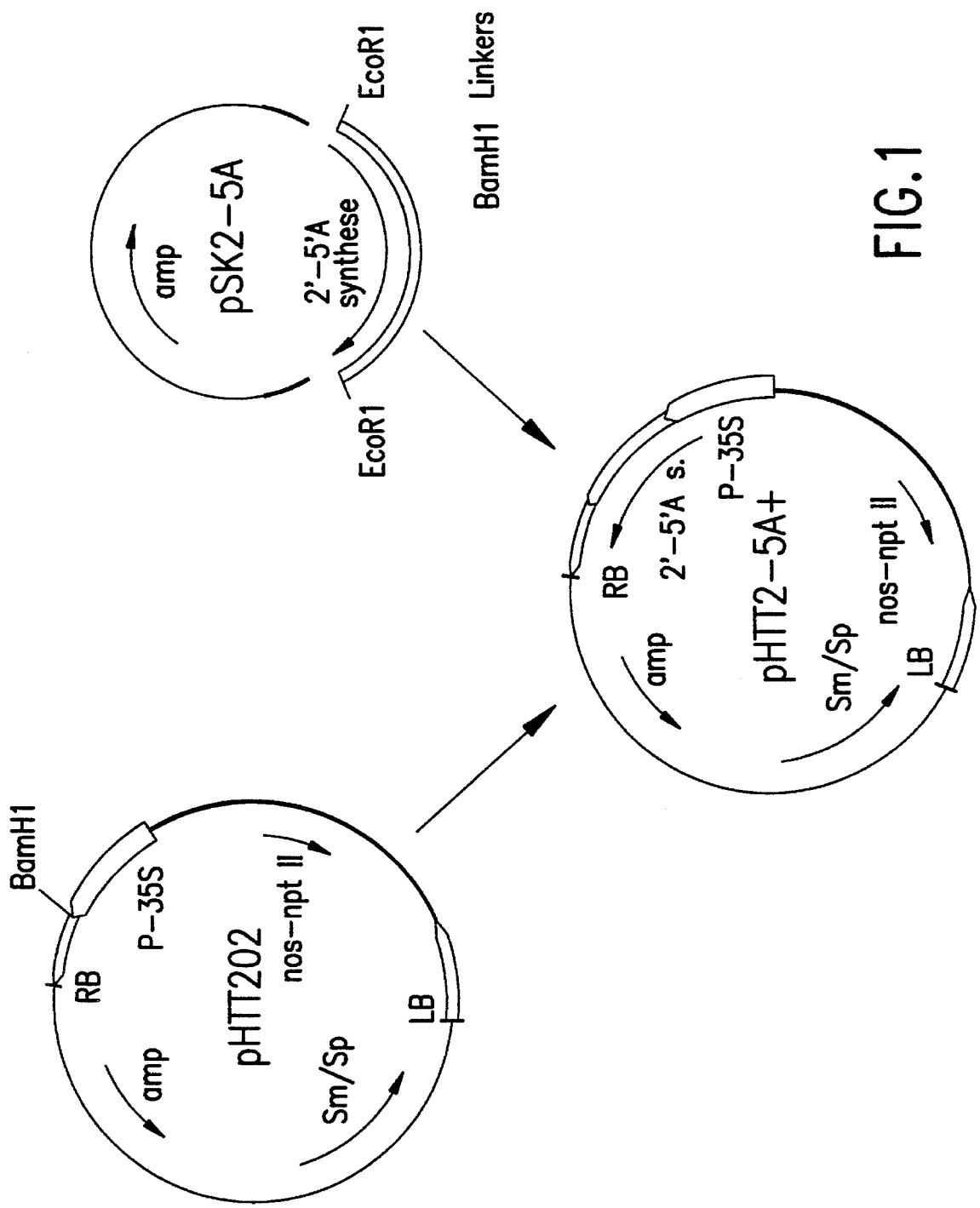
FIG. 1 is a schematic plasmid map showing construction of plasmid pHTT2,5A$^+$. The EcoRI fragment containing the rat 2,5A synthetase gene cDNA was excised from plasmid pSK2,5A$^+$, the cohesive termini were filled in and the obtained fragment was ligated into the BamHI site of vector pHTT202 using BamHI linkers. This results in the vector pHTT2,5A$^+$ containing the rat 2,5A synthetase gene under the control of the CaMV 35S promoter.
Figure 2:
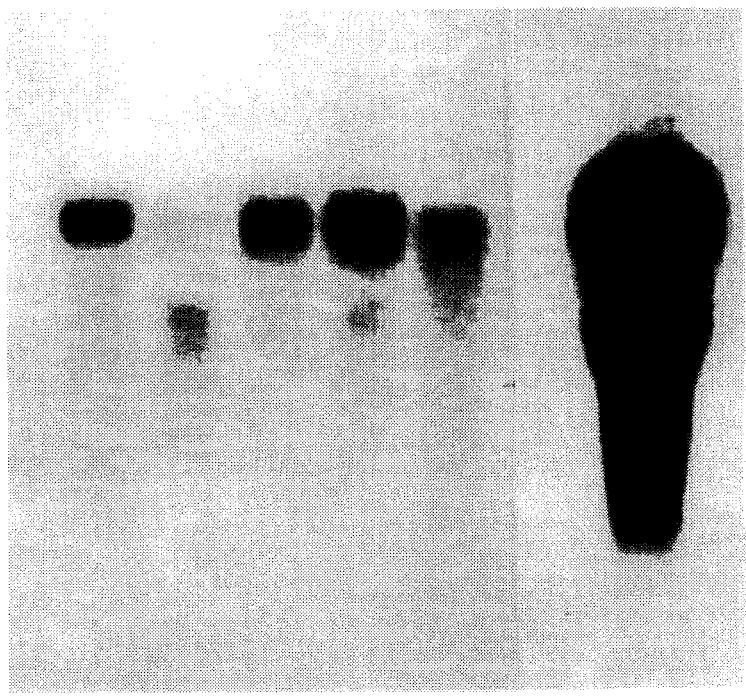
FIG. 2 is a photograph of a Northern blot analysis of total RNA from transgenic tobacco plants transformed with a 2,5A synthetase gene. 10 γg of total RNA per lane were probed with [$^{32}$P]-labelled 2,5A synthetase cDNA. Lanes 1–5 are transgenic tobacco lines and lane 6 is the rat 2,5A synthetase cDNA.
Figure 3A:
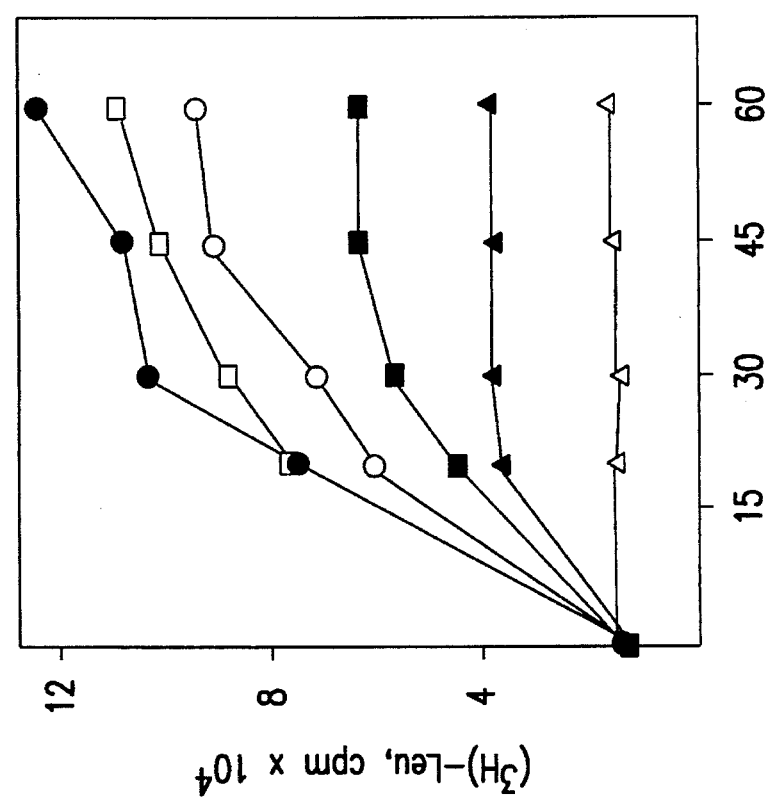
FIG. 3A shows the effect on trimers.
Figure 3B:
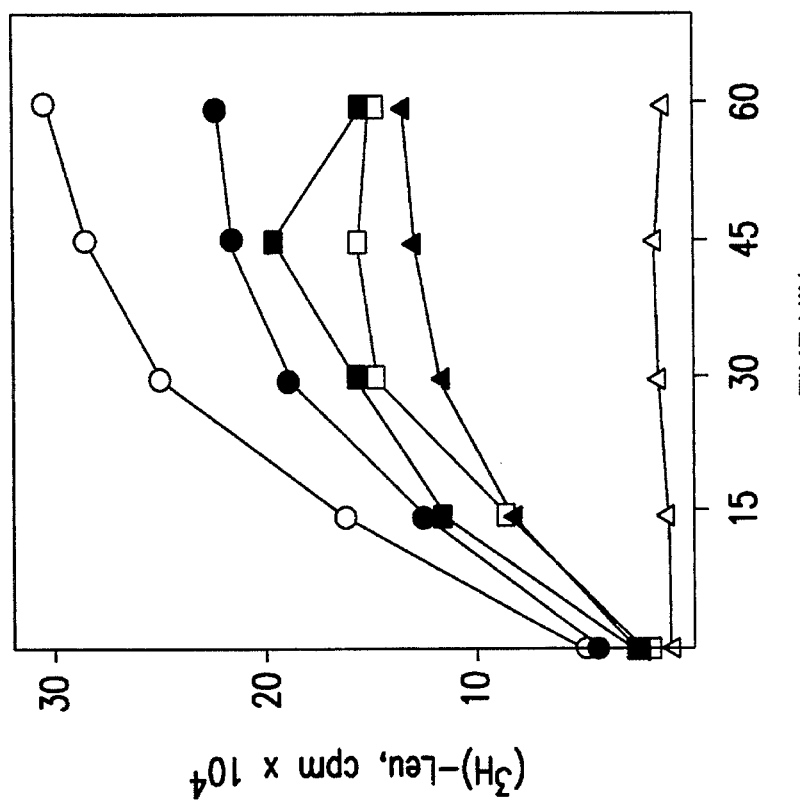
FIG. 3B shows the effect on tetramers. 0.8 γg of TMV-RNA were translated in vitro, the [$^{35}$S]-labelled proteins obtained from 5 γl samples were precipitated on glass fiber filters and then the incorporated radioactivity was measured: ●-without 2,5A; o-pppA$_n$; ■-ppA$_n$; □-pA$_n$; △-A$_n$; ▲-without RNA.
Figure 4:
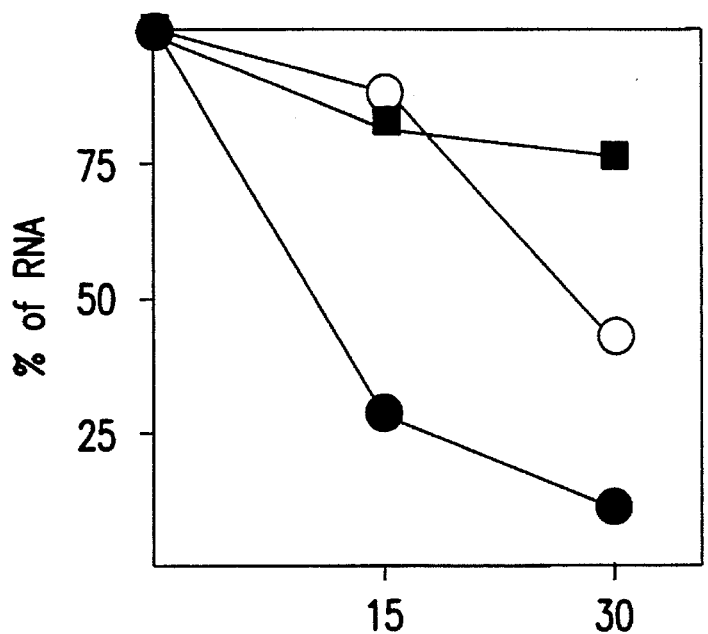
FIG. 4 is a graph showing the effect of different 2,5A trimers on TMV RNA degradation rate in wheat germ extract. TMVRNA was isolated from samples of wheat germ extract containing 1 γM 2,5A trimers, Northern blotted and hybridized with [$_{32}$P]-labelled TMV-cDNA. The amount of RNA was estimated from autoradiographs by laser densitometer: ■-without 2,5A; o-pppA$_3$; ●-A$_3$.

This invention provides a method for obtaining transgenic plants displaying resistance to multiple viral taxonomic groups by restoring to said plants a functioning 2,5A oligoadenylate pathway. In particular, plants containing parts of the 2,5A oligoadenylate pathway are genetically engineered to contain a DNA sequence encoding at least one polypeptide having a 2,5A synthetase activity. By this means a step in the 2,5A oligoadenylate pathway heretofore believed to be missing in all plants is provided, so that viral infection in the transgenic plants is inhibited via a 2,5A dependent endonuclease. Moreover, this invention relates to a process for the production of said transgenic plants by transfection with a genetically engineered DNA sequence encoding at least one polypeptide having a 2,5A synthetase activity.

The term "resistance to multiple viral taxonomic groups" refers to transgenic plants which are substantially resistant to a variety of viral taxonomic groups, such as potex-, carla- and tobamoviruses.

The term "genetically engineered DNA sequence" refers to a DNA sequence which has been manipulated by genetic engineering methods such as recombinant DNA techniques known to those of skill in the art.

The term "polypeptide having a 2,5 synthetase activity" refers to any polypeptide which is capable of enzymatically synthesizing 5'-dephosphorylated or phosphorylated 2,5-oligonucleotides with three or more adenosine residues such as $2,5A_3$, which is a trimer of adenylate linked by 2',5'-phosphodiester bonds, and is dephosphorylated at its 5'-end.

The term "endonuclease causing degradation of viral RNA" refers to a heterologous or homologous endonuclease which is capable of degrading viral RNA by enzymatic cleavage. Said endonuclease is activated by a 2,5A which is synthesized by a polypeptide having a 2,5A synthetase activity.

In a preferred embodiment of the present invention said DNA sequence or at least one part of said DNA sequence is homologous or heterologous to said transgenic plant.

In a further embodiment of the present invention said DNA sequence is a chimeric DNA sequence.

In a further preferred embodiment of the present invention said DNA sequence additionally encodes at least one selectable marker and/or at least one further polypeptide such as said endonuclease.

In a preferred embodiment of the present invention the DNA sequence encoding said polypeptide derived from a mammalian gene, a plant gene or a microorganism gene or is a synthetic gene.

In a particularly preferred embodiment of the present invention the DNA sequence encoding said polypeptide is a rat 2,5A synthetase gene (see FIG. 1) described in E. Truve, et al., Bio/Technology, 11:1048–1052, 1995.

In a preferred embodiment of the present invention said endonuclease is a latent plant RNA (RNAse L).

The expression of said polypeptide is under the control of an inducible or a constitutive promoter functioning in plants and allowing an induced and/or increased expression of said polypeptide. Examples of such promoters are cauliflower mosaic virus 35S-promoter, rice actin promoter, rbc S promoter from different species, Agrobacter TR2' promoter, phaseolin gene promoter or the NOS promoter. In a preferred embodiment of the present invention, the expression of the 2,5A synthesizing polypeptide is under the control of the cauliflower mosaic virus 35S-promoter.

The transgenic plant is a monocotyledoneous or a dicotyledoneous plant that utilizes the 2,5A oligoadenylate pathway. In a preferred embodiment of the present invention the transgenic plant is tobacco, rice, wheat, barley, maize, tomato, cucumber, soya, sweet potato, grapes, rapeseed, sugar beat, cotton, tea, sunflower, strawberry, rose, chrysanthemum, sweet pepper or potato.

A further object of the present invention is a propagating material derived from a transgenic plant displaying resistance to multiple viral taxonomic groups.

The term "propagating material" refers to intact plants or differentiated or undifferentiated plant tissue such as root, stem, leaf, callus, protoplast, suspension cultures and seeds.

A further object of the present invention is a process for the production of a transgenic plant displaying resistance to multiple viral taxonomic virus groups comprising the introduction of a genetically engineered DNA sequence encoding at least one polypeptide having a 2,5A synthetase activity, into the genetic material of a suitable plant.

The term "genetic material" refers to the nuclear genome of a plant cell, an organelle genome of the plant cell or an extrachromosomal form.

The term "introduction" refers to a method which is capable of introducing said genetically engineered DNA sequence into said genetic material of a plant cell. Preferred examples of said method are Agrobacterium-mediated transfer, plant virus mediated-transfer, microinjection, microprojectile bombardment, electroporation, PEG-mediated transformation and transformation of plant protoplasts with virus-based stable vectors.

In a preferred embodiment of the present invention said DNA sequence is contained in a vector under the control of a promoter allowing its expression in said transgenic plant.

In a particularly preferred embodiment of the present invention said vector is pHTT2,5A$^+$ which has been deposited under the requirements of the Budapest treaty at the "Deutsche Sammlung fur Mikroorganismen (DSM)" Braunschweig, Germany under the accession number DSM 6815. A culture of this plasmid has been deposited under the provisions of the Budapest Treaty on the International Recognition of the Deposit of Microorganisms for the Purpose of Patent Procedure and the Regulations thereunder (Budapest Treaty) and under conditions that assure maintenance of a viable culture for 30 years from the date of deposit, or for the enforceable life of the patent, or for a period of five years after the date of the most recent request for the furnishing of a sample of the deposited material, whichever is longest. Upon issuance of a patent, all restriction on the availability of the cultures to the public will be irrevocably removed. The organism will be made available during pendency of the patent application to one determined by the Commissioner to be entitled thereto under 37 C.F.R. 1.14 and 35 U.S.C. 122. The deposits were viable at the time of deposit. If the cultures are lost or destroyed, the cultures will be replaced in the respective depository for the period stated above.

In a further preferred embodiment of the present invention said introduction is carried out by transfection using the Agrobacterium system.

A further object of the present invention is the use of a genetically engineered DNA sequence encoding at least one polypeptide having a 2,5A synthetase activity, for the production of a transgenic plant displaying resistance to multiple viral taxonomic groups.

The following examples illustrate the invention. Further explanations of the molecular biological methods applied can be found in Sambrook, et al., "Molecular Cloning: A Laboratory Manual", supra.

EXAMPLE 1

A. Construction of the 2,5A gene containing plasmid cHTT2-SA+

Rat 2,5A synthetase cDNA was isolated from a rat hippocampus cDNA library in the vector λgt10 according to Amersham protocols using mouse 2,5A synthetase cDNA as a probe. cDNA was subcloned into the EcoRI site of pBluescript SK+ (Stratagene) expression vector. The resulting plasmid was named pSK2,5A. For transformation of tobacco plants, rat 2,5A synthetase cDNA was subcloned into the plant expression vector pHTT202. cDNA was excised from pSK2,5A by EcoRI, the cohesive termini were filled in and the cDNA was cloned into BamHI-linearized pHTT202 using synthetic BamHI linkers (FIG. 1). The resulting plasmid pHTT2,5A+ was used to transform Agrobacterium cells.

B. Transformation of Agrobacterium with the plasmid PHTT2-5a+

The plasmid pHTT202 is largely based on plasmid pBR322 sequence. pBR322-based cloning vectors are normally not mobilized from the host cell to another bacterium but they contain the "basis of mobilization", the bom site. When "helper" functions encoded by mob genes of helper plasmids are provided, the pBR322-based cloning vectors are also mobilized. For this purpose biparental mating based on the system described by Van Haute, et al., *EMBO J.*, 2:411–417, 1983, was used.

*E. coli* containing plasmid pHTT2,5A+ ($amp^R$, $spc/str^R$) was mated on L-plates with *E. coli* helper strain GJ23, which contains the Iα-type plasmid R64drd11 ($tet^R$, $str^R$) for the necessary tra functions and a second helper plasmid pGJ28 ($kan^R$, neoR) providing mob functions in trans to complement transmission of pBR-based mob $bom^+$plasmids.

The cells with helper plasmids were selected on L plates containing ampicillin, tetracyclin and kanamycin. These cells were cocultivated in L-broth with *Agrobacterium tumefaciens* strain C58C1 containing Ti-plasmid pGV2260 ($rif^R$, $cb^R$) where the genes responsible for tumorigenesis in the plant cell have been replaced by pBR322 sequences. Conjugated Agrobacterium cells were selected on plates containing rifampicin, spectinomycin and streptomycin. Since pBR322-based vectors cannot replicate in Agrobacterium, only Agrobacteria where recombination between the pBR322-sequence of pGV2260 and pHTT202 has lead to the formation of a cointegrate molecule can grow on selective plates. In order to confirm that T-DNA of recombinant plasmids contains the 2,5A synthetase gene, total DNA of resulting Agrobacteria was isolated (Dhaese, et al., *Nucl. Acids Res.*, 7:1837–1849, 1979) and analyzed by Southern blotting.

EXAMPLE 2

Transformation of tobacco plants with 2,5A synthetase gene

Figure 6:
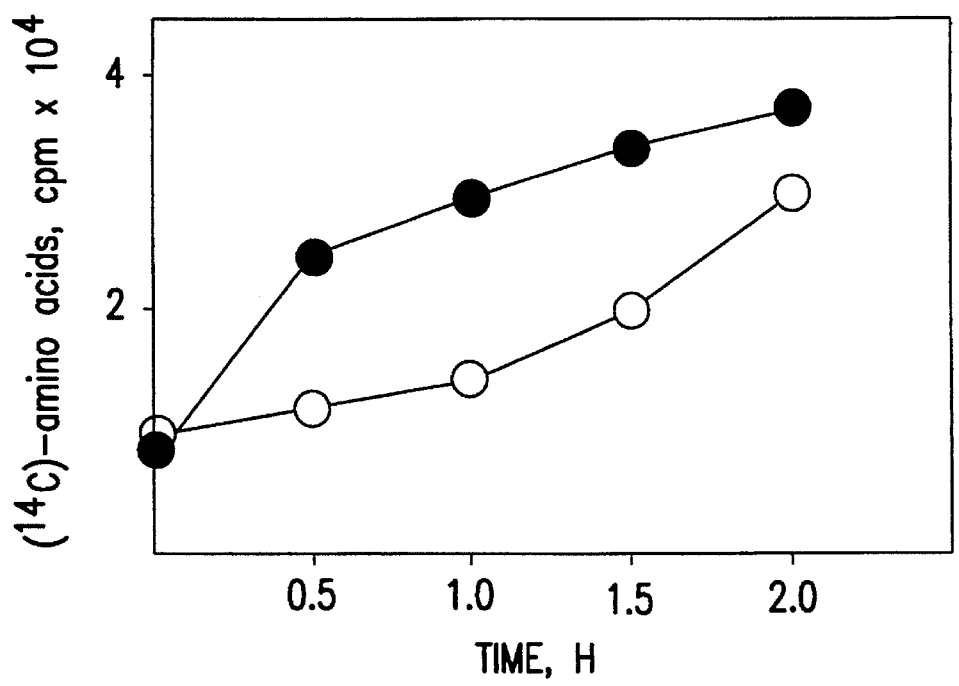
FIG. 6 is a graph showing the effect of 2,5A trimer "core" on protein synthesis in tobacco protoplasts. [$^{14}$C]-labelled protein hydrolysate was added to a tobacco protoplast culture and total radioactivity of cells was measured: ●-without 2,5A; o-1γM A$_3$.
Figure 5:
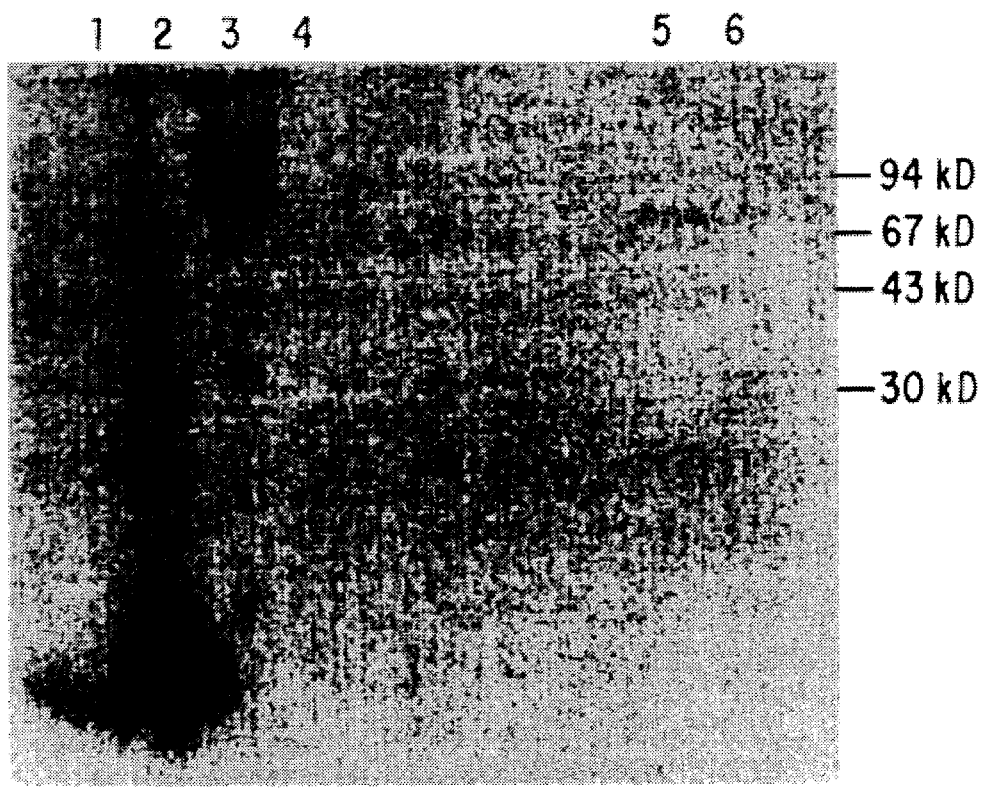
FIG. 5 is a photograph showing binding of 2,5A to plant cell extract proteins. [$^{32}$P]-labelled 2,5A was covalently crosslinked to proteins of cell extracts by the NaIO$_4$-oxydation method and separated on 12% SDS-PAGE electrophoresis. Lane 1 is rabbit reticulocyte lysate (prepared according to Sambrook, et al., "Molecular Cloning: A Laboratory Manual", *Cold Spring Harbor Laboratory, Cold Spring Harbor Laboratory Press* (1989)), lane 2 is mouse L cell extract with unlabelled 2,5A, lane 3 is mouse L-cell extract, lane 4 is rabbit reticulocyte lysate (Amersham), lane 5 is potato leaf extract and lane 6 is potato leaf extract with unlabelled 2,5A.

Transgenic *Nicotiana tabacum* SR1 plants were obtained via Agrobacterium-mediated transfer (Zambryski, *Annu. Rev. Genet.*, 22: 1–30, 1988). The method is based on the phenomenon that Agrobacterium stably transfers a segment of its Ti-plasmid into a plant genome upon contact with wounded plant cells. The segment called "T-DNA" is defined by its conserved border sequences. The genetic information between the border sequences can be replaced without affecting the efficiency of T-DNA transfer.

Transformation of tobacco plants with the 2,5A synthetase gene was carried out according to Horsch, et al. (*Science*, 227:1229–1231, 1985). *N. tabacum* SR1 leaves from plants grown on MS/2 medium (Murashige and Skoog, *Phys. Plant*, 18:473–497, 1962) in sterile conditions at 24° C. for 16 hour photoperiods were placed upside down in K3-400 mM sucrose medium (Nagy and Maliga, Z. *Pflanzenphysiol.*, 78:453–455, 1976) and cut in 0.5–1 $cm^2$ pieces so that all edges were cut. Agrobacterium with cointegrate T-DNA grown in M9 minimal medium (Sambrook, et al., supra) was added to K3-400 mM sucrose medium and dishes were kept for three days under the same conditions as for plants. Untransformed SR1 leaves were used as a control. The leaf discs were washed and transferred upside down to solid LS medium (Linsmaier and Skoog, *Phys. Plant*, pp.100–127, 1965) containing Claforan to kill Agrobacteria, benzylaminopurine (BAP) to induce shoots from leaf discs and kanamycin to select for the transformed cells because the segment of plasmid pHTT2,5A+ cointegrated in T-DNA of pGV2260 also contained the nos-npt2 gene conferring kanamycin L resistance to the transformed cells. After shoots appeared, they were cut and rooted on similar medium without BAP. Fully rooted plants were kept on MS/2 medium under the conditions described above.

In order to verify that plants were true transformants, total DNA and RNA from leaf tissue was isolated according to Dellaporta, et al., *Plant Mol. Biol. Rep.*, 1:19–21, 1983 and Verwoerd, et al., *Nucl. Acids Res.*, 17:2362, 1989, respectively. Southern and Northern blotting analysis was carried out according to Amersham protocols using [$^{32}$P]-labelled 2,5A synthetase cDNA as a probe (FIG. 2).

EXAMPLE 3

Identification of 2,5A dependent RNase activity

Studies on the effect of different 2,5 oligoadenylate forms by tobacco mosaic virus (TMV) in vitro translation in wheat germ extract (WGE) show that nonphosphorylated tri- and tetramers of 2,5A can efficiently inhibit TMV RNA translation in WGE (FIG. 3). The degradation rates of TMV RNA during in vitro translation in the presence and absence of 2,5A were analyzed by taking samples from the translation mixture and isolating RNA as described by Toots, et al., (*Mol. Biol.* (USSR) 22:1473–1481, 1988. After electrophoresis in agarose/formamide gel and Northern blotting, the concentration of RNA in the samples was estimated by scanning the autoradiographs of [$^{32}$P]-labelled filters with a laser densitometer. As shown in FIG. 4, Addition of 2,5A trimer "core" led to a rapid degradation of TMV RNA, whereas the degradation rate of TMV RNA was much lower in control experiments with or without triphosphorylated 2,5A. In conclusion, the inhibitory effect of the 2,5A "core" on in vitro translation in plant cell-free extract is caused by rapid degradation of substrate RNA.

In order to identify 2,5A-binding proteins in plant extracts, 2,5A was ligated to [$^{32}$P]pCp as described by Knight, et al. (*Methods in Enzymology*, 79:216–227, 1981). [$^{32}$P]-labelled 2,5A was covalently crosslinked to proteins of potato cell extracts by the $NaI0_4$ oxidation method according to Wreschner, et al. (*Eur. J. Biochem.*, 124:261–268, 1982). The specificity of binding was controlled in a competition assay where the unlabelled 2,5A was added in excess to reaction mixtures. The reaction mixtures were separated by 12% SDS-polyacrylamide gel electrophoresis (SDS-PAGE).

As shown in FIG. 5, A 70 kD protein was identified in potato leaf extracts which specifically bound to labelled 2,5A. The specificity of binding was shown in the competition assay where unlabelled 2,5A completely displaced [$^{32}$P]2,5A in potato extracts (FIG. 5).

Since 2,5 A-induced inhibition of in vitro translation in WGE was caused by rapid degradation of TMV RNA, the 70 kD 2,5A-binding protein from plant extract is a 2,5A-activated plant endoribonuclease.

The effect of 2,5A on protein synthesis in N. tabacum SR1 protoplasts was also tested. Protoplasts were obtained according to Honkanen, et al., "Biotechnology in tropical crop improvement: proceedings of the international biotechnology workshop", (1988) from the leaf mesophyll of plants grown under sterile conditions and maintained in K3-400 mM sucrose medium. After adding [$^{14}$C]-labelled amino acid hydrolysate, samples were collected from the protoplast mixture to analyze the concentration of de novo synthesized proteins. Proteins were precipitated by trichloroacetic acid and incorporated radioactivity was measured. As shown by the data in FIG. 6, 2,5A efficiently inhibited protein synthesis in tobacco protoplasts, which again indicates the 2,5A action as a protein synthesis inhibitor in plant systems in vivo.

Having identified a 2,5A dependent RNASE activity in potato and tobacco it can be concluded that there is a metabolic pathway in plants which partially resembles the IFN-induced metabolic pathway of mammals that causes a viral resistance.

EXAMPLE 4

Propagation of potato viruses X and S and tobacco mosaic virus in 2,5A transgenic plants.

In order to examine the propagation of different viruses in transgenic plants expressing 2,5A synthetase, various infection experiments were carried out. For the transformation of tobacco and potato plants a 2,5A synthetase cDNA was cloned between the cauliflower mosaic virus 35S promoter and the T-DNA gene 7 polyadenylation signal of the plant expression vector pHTT202. The transferred segment of the vector also contained the hybrid nopaline synthetase-neomycin phosphotransferase II (nos-nptII) gene giving kanamycin resistance.

Construction of plasmid vectors.

Rat 2,5A synthetase cDNA was excised from pSK2,5A by NotI, the cohesive termini filled in, and the cDNA ligated to the BamHI-linearized plant expression vector pHTT202 using synthetic BamHI linkers. The resulting plasmids were named pHTT2,5A+ and pHTT2,5A-indicating the sense or antisense orientation of the 2,5A synthetase cDNA insert, respectively. 2,5A synthetase cDNA was integrated into the *Agrobacterium tumefaciens* Ti-plasmid pGV2260 via homologous recombination. Recombinant Agrobacterium was verified by isolating total bacterial DNA and carrying out Southern analysis.

Transformation and regeneration of tobacco and potato.

*Nicotiana tabacum* L cv. Petite Havana SR1 and virus-free *Solanum tuberosum* L. cv. Pito (obtained from The Seed Potato Center of Agricultural Research Centre of Finland, Tyrnava) were propagated and rooted on MS medium without hormones. Isolates of PVX, PVS, and PVY were obtained from NPF Biotekhtsentr, Korenevo, Moscow Region, Russia or from The Institute of Plant Protection, Jokioinen, Finland Leaf discs from nicotiana tabacum L. SR1 plants were cocultivated with Agrobacterium according to Horsch, et al., (*Science*, 227:1229–1231). Shoots were induced from the transformed discs with a diameter of 8 mm kept upside down in sterile water at 24° C. under 16 hour photoperiods for up to 5 days. Roots were induced, and fully rooted plants were grown as described earlier. Stem pieces of *Solanum tuberosum* L. were cocultivated for two days with Agrobacterium. Shoots were induced with MS medium containing Claforan (500 µg/ml), supplied with BAP 2.25 µg/ml and 1-naphtaleneacetic acid 0.03 µg/ml during the first two weeks and later with BAP 0.5 µg/ml and gibberellic acid 0.5 µg/ml from Agrobacterium-transformed tobacco and potato cells. For selection, 100 µg/ml kanamycin was added. To select for true transformants, total DNA and RNA from tobacco and potato leaf tissue was isolated, and Southern and Northern analyses were carried out. Nylon membranes (Amersham, Arlington Heights, Ill.) were hybridized with the radioactive 2,5A synthetase probe at 42° C. with 50% formamide and 1M NaCl and washed in high stringency conditions (10 min with 15 mM NaCl and 0.1% sodium dodecylsulfate at room temperature).

Infection of tobacco and potato with various plant viruses.

Plants expressing detectable amounts of the 2,5A synthetase mRNA were used for the virus infection experiments. In a series of independent experiments transgenic tobacco plants were infected with potato virus X (PVX), potato virus S (PVS), and potato virus Y (PVY), belonging to the potex-, carla- and potyvirus groups, respectively. Tobacco plants were transferred to soil two weeks prior to the infection. For the infection, 1–2 lower leaves of plants with 6–8 leaves were treated with carborundum, 10 µg of purified virus in 5 mM Na-phosphate buffer, pH 7.2 was manually inoculated onto the leaf surface, and carborundum washed away after 30 minutes with sterile water. Plants were kept for 24 hours in darkness and subsequentially as before infection. Samples were collected by taking one of the top leaves every fifth day and freezing it in liquid nitrogen. Micropropagated potato plantlets were grown for 4–5 weeks in vivo before infection in the greenhouse and 6 weeks before infection in the field. Fully opened leaflets for inoculation were selected in the middle part of the plants. Juice from PVX- or PVY-infected *N. glutinosa* leaves were used in infection. For PVX the juice was diluted 1:2500 and for PVY 1:4 (in 50 mM NA-phosphate buffer, pH 7.0). After treating three randomly selected potato leaflets (of 4–6 week old, 20–25 cm high plants at 6 leaves stage) with carborundum, the diluted sap was spread over them. As a sample, three leaflets from fully opened (with 5–7 leaflets) topmost leaves were collected and analyzed immediately.

Detection of virus concentration in infected plant leaves.

Tobacco leaf samples were homogenized in a mortar, adding 1 ml of the immunoassay buffer per gram of leaf material. Virus concentrations were estimated as described in Example 3 herein using 21 XD2 monoclonal antibodies (MAbs) and a time-resolved fluoroimmunoassay for PVX detection, and S4A4 MAbs and DAS-ELISA for PVS detection. The PVY concentration in tobacco was measured using a commercial PVY enzyme immunoassay kit from Boehringer Mannheim. For PVX-detection in potato, leaflets were homogenized in 1 ml immunoassay buffer (Boehringer Mannheim) per g of leaf tissue in plastic bags. Extract was diluted into cold sample buffer (1:5000) and analyzed by using ELISA (Boehringer Mannheim PVX kit). For quantification a purified PVX virus preparation was used. Juice extract from PVY-infected potato leaves was obtained by using a special pressure apparatus (MEKU, E. Pollahne, Germany) and the extract was diluted into cold sample buffer (1:4). Antisera for PVY analyses was produced in rabbits in Agricultural Research Centre and IgG was conjugated with alkaline phosphatase, and ELISA test was carried out. Statistical analyses were performed using ANOVA (PVX greenhouse data), nested design and ANOVA (PVY data).

Figure 7:
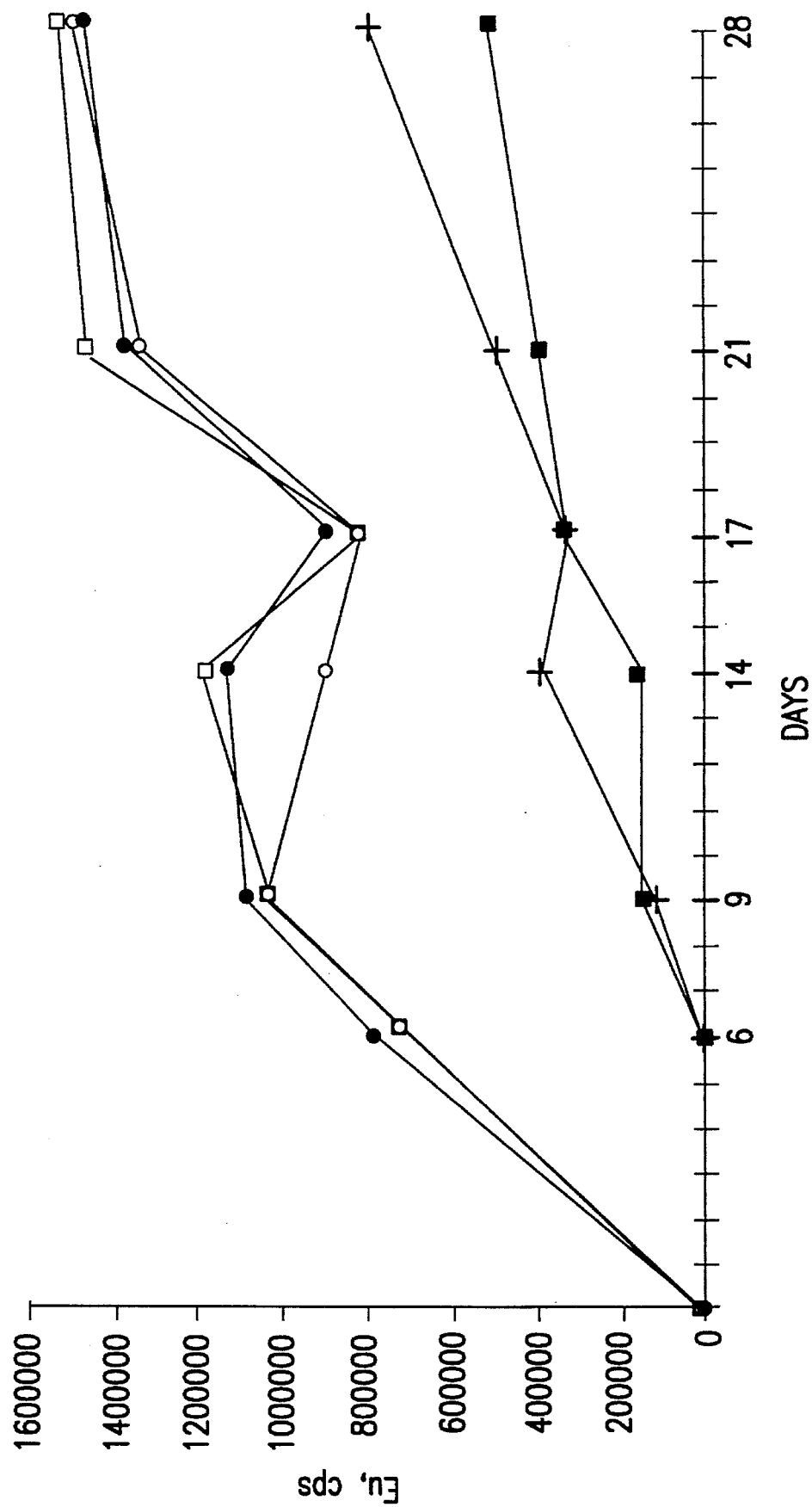
FIG. 7 is a graph showing the concentration of infecting PVX virus in transgenic tobacco plants containing the 2,5A synthetase gene. Intact nicotiana tabacum L. SR1 tobacco plants were infected with 10γg/ml PVX and leaf samples from one of four independently generated individual transgenic clones (4N1–4N12) were analyzed by time resolved fluoroimmunoassay (TRFIA) using 21XD2 antibodies and 21XD2 europium (Eu) conjugate. The virus concentration was determined by Eu fluorescence counts per-second: ●-nicotiana tabacum L. SR1 control; o-4N1; □-4N5; +-4N11; * -4N12.
Figure 8:
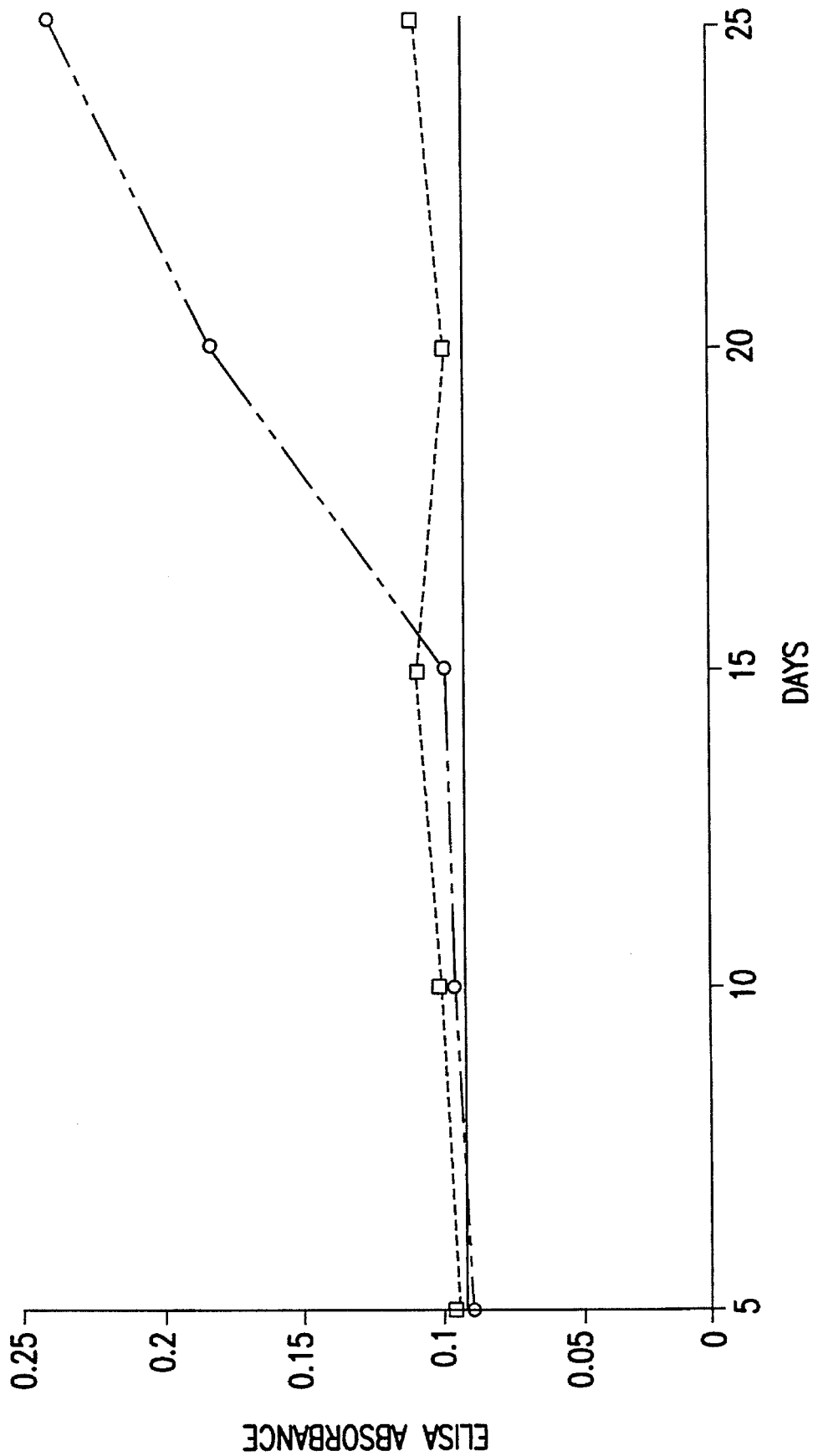
FIG. 8 is a graph showing propagation of PVS in transgenic tobacco plants containing the 2,5A synthetase gene. Intact plants were infected with 10γg/ml PVS, and leaf samples were analyzed by ELISA using S4A4 antibodies and S4A4 horse radish peroxidase conjugate. The virus concentration is determined by optical density of color reaction at 450 nm: o-nicotiana tabacum L. SR1 control; □-transgenic plants with 2,5A synthetase gene in "sense" orientation, ——ELISA background.

Experiments were carried out on four intact clones or plants lines and for each individual clone, 12 plants were tested and the data were summarized. A total of 12 independent transgenic tobacco clones derived from the fourth transformation and selected for containing a full-length rat 2,5A synthetase cDNA (2,5A+ tobacco plants) were obtained and numbered 4N1, 4N2, 4N3, 4N4, 4N5, 4N6, 4N7, 4N8, 4N9, 4N10, 4N11, and 4N12. Unless indicated otherwise, three plants from each clone were tested in parallel. In FIG. 7 is shown the resistance data of one control untransformed SR1 plant line and clones 4N1, 4N5, 4N11 and 4N12, representative individual transgenic tobacco clones containing a full-length 2,5A synthetase cDNA derived from the fourth of four independent transformations. Individual clones were randomly picked as representative from those clones exhibiting antibiotic resistance, integration of 2,5A synthetase cDNA in the tobacco genome as verified by Southern blotting, and the level of mRNA expression of the 2,5A synthetase as verified by Northern blotting. In some cases the 2,5A synthetase protein was also detected by ECL Western blotting.

In addition, a transgenic potato clone expressing 2,5A synthetase antisense RNA was constructed. From putative transformants of potato, 7 morphologically normal plantlets numbered P1, P2, P3, P4, P5, P6 and P7 were selected for further tests. Sequences homologous to rat 2,5A synthetase were not found either in nontransformed tobacco or potato plants using high stringency hybridization and washing conditions.

The expression of 2,5A synthetase mRNA was analyzed with Northern blots. All transgenic clones expressed detectable amounts of 2,5A synthetase mRNA although their expression levels were different. One transgenic tobacco clone (T4) expressed as a major product a truncated form of 2,5A synthetase mRNA.

The propagation of PVX, PVS and potato virus Y (PVY) in plants expressing 2,5A synthetase was followed for one month post infection. Plants transformed with 2,5A synthetase cDNA in antisense orientation or nontransformed tobaccos were used as control plants. As these two taxonomic groups of plants did not exhibit any difference in respect of susceptibility to the virus infection in any of the experiments carried out, their infectivity data are in the following taken together and referred to as "control plants." The tobacco plantlets were infected about two weeks after the transfer to the soil at the 6–8 leaves stage. Morphologically the transgenic plantlets looked normal and were undistinguishable from the nontransformed tobaccos of the same age.

In eight tobacco clones, the concentrations of the virus and the dynamics of infection were similar to that of nontransgenic control plants. In clones 4N11 and 4N12 and to a certain extent in clone 4N1, inhibition of PVX replication during the first two weeks post infection was observed. In one clone (4N12), the virus concentration was much lower throughout the experiment. Moreover, in this clone propagation of PVX was detected 1–2 weeks later than in control plants. One month after infection with PVS (carlavirus group) all twelve transgenic 2,5A+ clones (including clone 4N12 showing low levels of PVX replication) contained PVS at levels scarcely detectable with DAS-ELISA, whereas in control (TC) tobaccos PVS was clearly present. All transgenic plants with 2,5A synthetase in sense orientation were resistant to PVS infection. There were no visible symptoms in either PVX or PVS infected tobaccos for either the transgenic or control plants. As *N. tabacum* is not a common host plant for PVS, the absence of symptoms was expectable in this case.

Figure 9:
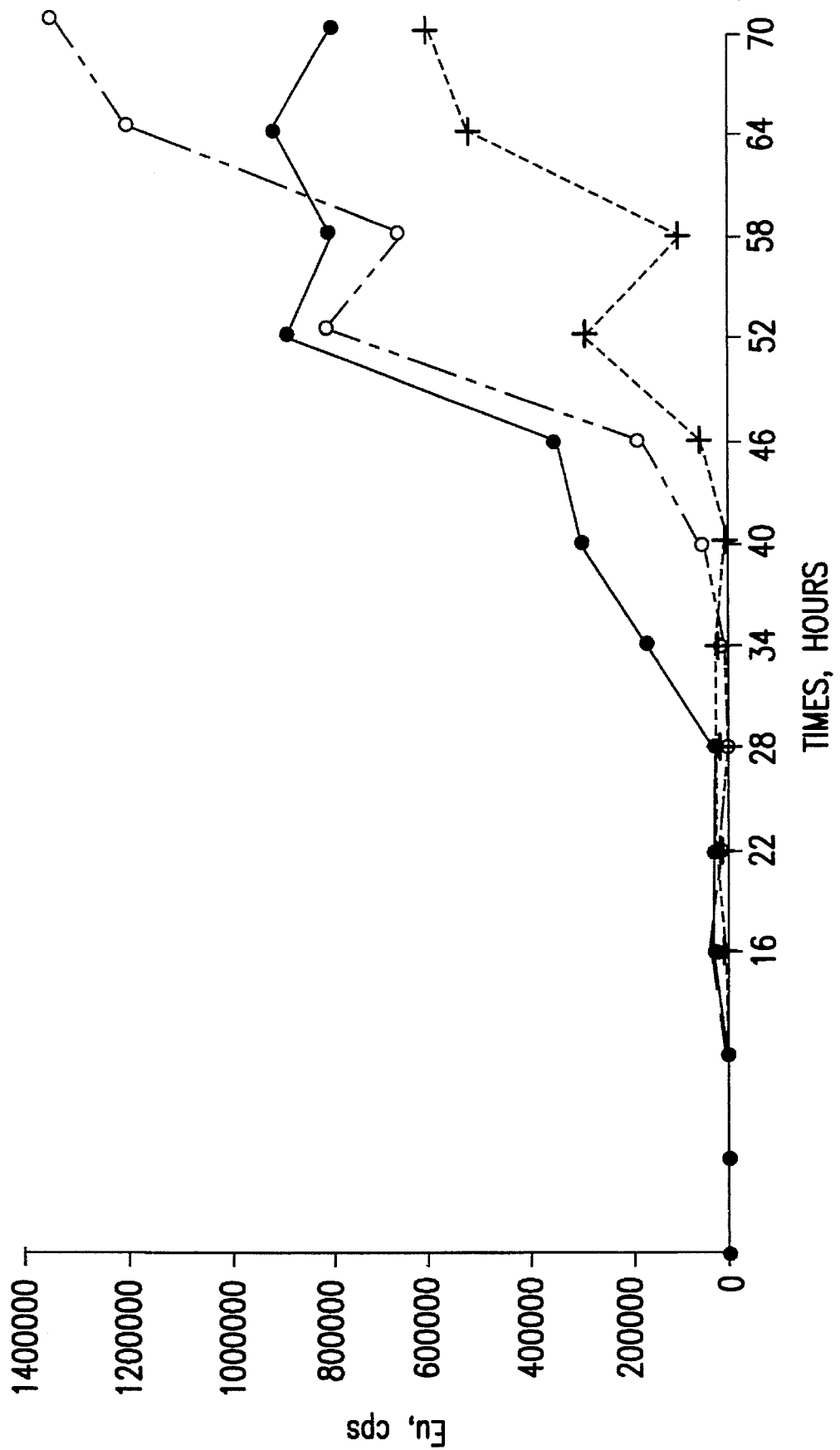
FIG. 9 is a graph showing propagation of PVX in leaf discs of transgenic plants containing the 2,5A synthetase gene. Leaves were infected with 10γg/ml PVX, discs with 8mm diameter were punched out and kept in sterile water. The discs were analyzed as PVX-infected intact plants (see FIG. 7): ●-nicotiana tabacum L. SR1 antisense transformed and untransformed controls; o-4N10; +-4N12.

FIG. 9 presents the data of leaf disc experiments conducted to confirm the results of plant experiments. Only two transgenic plants and SR1 control plants were utilized in these experiments, since they are mere confirmatory in nature. The data in FIG. 9 confirm that clone 4N12, which was resistant in the full plant test (FIG. 7), is also resistant in the leaf disc experiment whereas SR1 control plants and clone 4N10 were not.

EXAMPLE 5

Detection of 2,5 oligoadenylates in transgenic plants

In order to detect the concentration of 2,5A in transgenic tobacco SR1 plants expressing 2,5A synthetase, leaf extracts from virus-infected and non-infected plants were prepared. A competition assay of unlabelled 2,5A from plant extracts with 2,5A[$^{32}$P]pCp was carried out. Mouse L-cell extract was used as a source for 2,5A-binding endoribonuclease L (RNase L). The mixture of labelled 2,5A, L-cell extract and leaf extract was incubated for 90 minutes on ice. Proteins from the mixture were precipitated on nitrocellulose filters and the radioactivity of filters and filtrate was counted. The mixture without plant extract was used as a positive control and the mixture where $10^{-7}$ M of unlabelled 2,5A trimer completely displaced the labelled 2,5A was used as a negative control.

The results shown in Table 1 indicate that non-infected transgenic plants expressing 2,5A synthetase contained low (if any) detectable amount of 2,5A similar to that of untransformed control plants and control transgenic plants carrying 2,5A synthetase gene in antisense orientation. This is because 2,5A synthetase is expressed as an inactive enzyme which can be activated by double stranded RNA. When transgenic plants expressing the 2,5A synthetase were infected with PVX, the 2,5A became detectable and its intracellular concentrations were even higher than in control mixtures. Such an increase of 2,5A was not detected in SR1 control plants. The increase of 2,5A in transgenic plants results in inhibition of PVX-, PVS- and TMV-propagation.

TABLE 1

Competitive radiobinding assay for the determination of the concentration of 2,5 oligoadenylates in 2,5A synthetase transgenic plants pre- and postinfection with PVX

| Plants | Normalized % of the filtrate (pos. control without plant material is taken as 100%) |
|---|---|
| Control SR1 | 29.2 |
| Transgenic 2,5A, antisense construct | 65.5 |
| Transgenic 2,5A, sense construct | 47.2 |
| Control SR1 × PVX | 54.6 |
| Transgenic 2,5A+ × PVX | 191.7 |
| Without plant extract | 100.0 |

As a conclusion, double stranded replicating intermediates of PVX RNA are able to activate the inactive 2,5A synthetase which results in the synthesis of intracellular 2,5A.

EXAMPLE 6

Detection of PVX infection in transgenic potato plants: Field test

Figure 10:
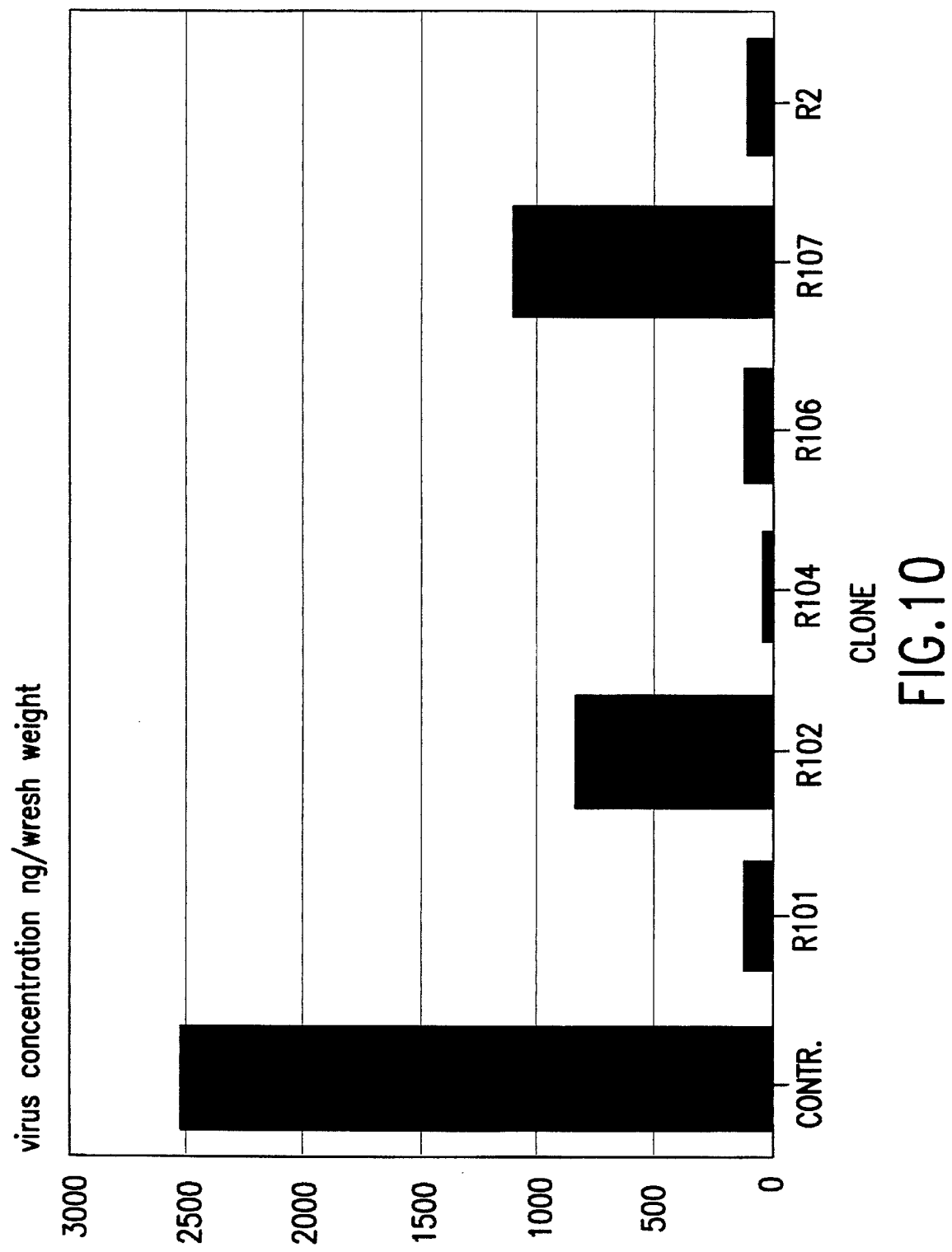
FIG. 10 is a bar graph showing virus concentration (PVX) in the field grown transgenic potato plants containing 2,5A synthetase genes. Intact plants were infected with sap fluid collected from PVX infected tobacco plants. Leaf samples were analyzed by ELISA, using immunodiagnostic kit for PVX (Boehringer Mannheim). The virus concentration after five weeks of infection was determined by optical density of color reaction at 405 nm. Contr.=control clone; R101, R102, R104, R106, R107 and R2=transgenic clones.

Intact potato plants containing the 2,5A synthetase gene were infected with sap fluid collected from PVX infected tobacco plants and grown in the field. Leaf samples were analyzed five weeks after infection by ELISA using an immunodiagnostic kit for PVX (Boehringer Mannheim). The virus concentration was determined by optical density of color formation at 405 nm (see FIG. 10).

The concentration of PVX in plants containing the 2,5 A synthetase gene was drastically reduced as compared to control plants.

The foregoing description of the invention is exemplary for purposes of illustration and explanation. It should be understood that various modifications can be made without departing from the spirit and scope of the invention. Accordingly, the following claims are intended to be interpreted to embrace all such modifications.

We claim:

1. A transgenic plant that utilizes the 2,5A oligoadenylate pathway and displays resistance to multiple plant viral taxonomic groups comprising a genetically engineered DNA sequence encoding at least one polypeptide having a 2,5A synthetase activity, wherein said polypeptide activates an endonuclease causing degradation of viral RNA.

2. The transgenic plant according to claim 1, wherein said DNA sequence is a heterologous DNA sequence.

3. The transgenic plant according to claim 1, wherein the coding sequence of said polypeptide is selected from the group consisting of a mammalian derived gene, a plant derived gene, a microorganism derived gene, and a synthetic derived gene.

4. A transgenic plant according to claim 1 wherein the plant virus is TMV.

5. A transgenic plant according to claim 1 wherein the plant virus is PVX.

6. A transgenic plant according to claim 1 wherein the plant virus is PVS.

7. A transgenic plant according to claim 1 wherein the plant virus is PVY.

8. The transgenic plant according to claim 3, wherein the coding sequence is rat 2,5A synthetase gene.

9. The transgenic plant according to claim 1, wherein the expression of said polypeptide is under the control of an inducible or a constitutive promoter.

10. The transgenic plant according to claim 1, wherein the plant is selected from the group consisting of maize, tomato, cucumber, soya, sweet potato, grape, rapeseed, sugar beet, cotton, tea, sunflower, strawberry, rose, chrysanthemum, sweet pepper and potato.

11. The transgenic plant of claim 1 wherein the DNA is derived from a rat 2,5A synthetase gene.

12. A propagating material derived from the transgenic plant according to claim 1.

13. A process for the production of a transgenic plant with resistance to multiple viral taxonomic groups comprising:
   A) preparing a genetically engineered DNA sequence encoding at least one polypeptide having a 2,5A synthetase activity;
   B) operably linking the DNA sequence to a promoter for said DNA;
   C) transforming a transformable, regenerable plant cell to contain the operably linked DNA sequence of step B); and
   D) regenerating said plant cell to produce a transgenic plant.

14. The process according to claim 13, wherein said DNA sequence is contained in a vector under the control of a promoter allowing its expression in said transgenic plant.

15. The process according to claim 14, wherein said vector is pHTT2,5A+ (DSM No. 6815).

16. The process according to claim 13, wherein said introduction is carried out by transfection using the Agrobacterium system.

17. A transgenic plant cell that utilizes the 2,5A oligoadenylate pathway and displays resistance to multiple plant virus taxonomic groups comprising a genetically engineered DNA sequence encoding at least one polypeptide having a 2,5A synthetase activity.

18. A plant cell according to claim 17 wherein the plant virus is a member of the RNA plant virus group.

19. A plant cell according to claim 17 wherein the plant virus is TMV.

20. A plant cell according to claim 17 wherein the plant virus is PVX.

21. A plant cell according to claim 17 wherein the plant virus is PVS.

22. A plant cell according to claim 17 wherein the plant virus is PVY.

23. A plant cell displaying resistance to multiple plant virus taxonomic groups descended from the plant cell of claim 17 and comprising said 2,5A synthetase activity.

24. A method for inhibiting viral infection in a plant comprising:
   A) preparing a genetically engineered DNA sequence encoding at least one polypeptide having a 2,5A synthetase activity;
   B) operably linking the DNA sequence to a promoter for said DNA;
   C) transforming a transformable, regenerable plant cell to contain the operably linked DNA sequence of step B).

* * * * *